United States Patent
Perez-Camargo et al.

(10) Patent No.: US 8,962,007 B2
(45) Date of Patent: *Feb. 24, 2015

(54) METHOD OF IMPROVING ABSORPTION OF VITAMIN E BY A PET ANIMAL

(71) Applicant: Nestec S.A., Vevey (CH)

(72) Inventors: Gerardo Perez-Camargo, St. Joseph, MO (US); Avinash Patil, St. Joseph, MO (US); Carolyn Jean Cupp, Liberty, MO (US); Armand Malnoe, Montaubion-Chardonney (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/908,615

(22) Filed: Jun. 3, 2013

(65) Prior Publication Data

US 2013/0295078 A1    Nov. 7, 2013

Related U.S. Application Data

(63) Continuation of application No. 10/509,951, filed as application No. PCT/EP03/03523 on Apr. 3, 2003, now Pat. No. 8,475,834.

(30) Foreign Application Priority Data

Apr. 5, 2002   (EP) ..................... 02076346

(51) Int. Cl.
| | | |
|---|---|---|
| A61F 13/00 | (2006.01) | |
| A61K 31/145 | (2006.01) | |
| A23K 1/16 | (2006.01) | |
| A23K 1/165 | (2006.01) | |
| A23K 1/175 | (2006.01) | |
| A23K 1/18 | (2006.01) | |
| A61K 31/194 | (2006.01) | |
| A61K 31/685 | (2006.01) | |
| A61K 35/60 | (2006.01) | |
| A61K 36/28 | (2006.01) | |

(52) U.S. Cl.
CPC ............ *A61K 31/145* (2013.01); *A23K 1/1603* (2013.01); *A23K 1/1631* (2013.01); *A23K 1/1634* (2013.01); *A23K 1/164* (2013.01); *A23K 1/1653* (2013.01); *A23K 1/175* (2013.01); *A23K 1/1846* (2013.01); *A61K 31/194* (2013.01); *A61K 31/685* (2013.01); *A61K 35/60* (2013.01); *A61K 36/28* (2013.01)
USPC ........................................... 424/422

(58) Field of Classification Search
None
See application file for complete search history.

(56) References Cited

U.S. PATENT DOCUMENTS

| | | | | |
|---|---|---|---|---|
| 4,759,933 A | * | 7/1988 | Uchida et al. | 426/7 |
| 5,087,473 A | * | 2/1992 | Leo | 426/646 |
| 6,471,999 B2 | * | 10/2002 | Couzy et al. | 426/2 |
| 6,524,619 B2 | * | 2/2003 | Pearson et al. | 424/472 |
| 2002/0119237 A1 | * | 8/2002 | Hevey | 426/601 |

* cited by examiner

*Primary Examiner* — Snigdha Maewall
(74) *Attorney, Agent, or Firm* — K&L Gates LLP

(57) ABSTRACT

A method of providing a pet with a benefit relating to effective assimilation of a lipid is described wherein the pet is administered, as a part of, or in addition to its regular diet, an edible composition that contains an ingredient that maintains, promotes or enhances the capacity of the pet to digest lipid efficiently. The invention extends to compositions for use in promoting lipid assimilation in pets, particularly senior or elderly pets. The compositions include pancreatic, liver and intestinal mucosa function-promoters. In embodiments, the liver function-promoter may be selected from taurine, emulsifiers, vitamins, minerals, glutathione and glutathione promoters.

3 Claims, 1 Drawing Sheet

Relationship between Fat digestibility (%) and Serum Vitamin E (ug/ml).
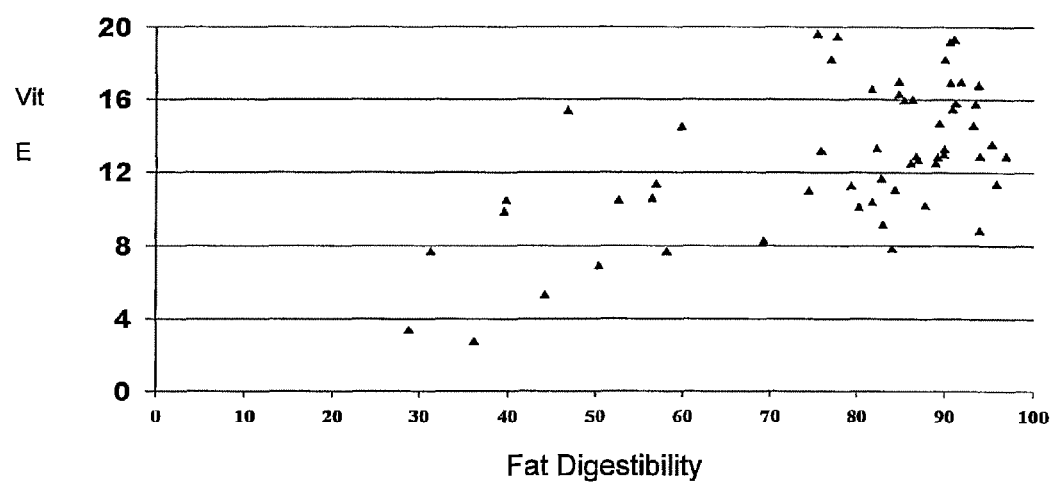

METHOD OF IMPROVING ABSORPTION OF VITAMIN E BY A PET ANIMAL

PRIORITY CLAIM

This application is a continuation of U.S. application Ser. No. 10/509,951, filed Oct. 4, 2004, which is a National Stage of International Application No. PCT/EP03/03523, filed on Apr. 3, 2003, which claims priority to European Application No. 02076346.2, filed Apr. 5, 2002, the entire contents of which are expressly incorporated herein by reference thereto.

FIELD OF THE INVENTION

This invention relates generally to methods of enhancing vitamin E absorption by pet animals. In particular, it relates to improving absorption of vitamin E in senior cats suffering the effects of pathologies and/or aging. The invention extends to a food and/or food supplement product and to its use in improving vitamin E absorption and/or assimilation in pet animals.

BACKGROUND

Vitamin E is a fat-soluble vitamin that is absorbed only with long chain fatty acids. A defect in either the absorption or digestion of lipid can therefore lead to deficiencies in this and other vitamins, due to their binding with unabsorbed fatty acids (Simpson, K W and Michel, K E. Micronutrient status in patients with gastrointestinal disease. Proceedings ACVIM, Denver, Colo., pp. 651-653, 2001). Hence, a pet with low lipid digestibility is susceptible to several potential nutritional deficiencies, which can compromise its health.

Studies on senior cat nutrition have shown that a significant number of older pets—such as those above the age of 9 years—exhibit a decreased capacity to digest fat. Several scientific publications have likewise reported an age-related decrease in lipid digestibility in cats (Burkholder, W J. Age-related changes to nutritional requirements and digestive function in adult dogs and cats. JAVMA, Vol 215, No. 5, Sep. 1, 1999; Nicholson A, Watson A D J. Mercer J R. Fat malassimilation in three cats. Australian Veterinary Journal, Vol. 66, No. 4, April 1989; Peachey S E, Dawson J M, Harper E J. The effects of aging on nutrient digestibility by cats fed beef tallow, sunflower oil or olive oil enriched diets).

There can be any of a number of pathologies that can lead to poor digestibility of lipids. Malabsorption and maldigestion can occur from almost any diffuse disease of the intestine, from exocrine pancreatic insufficiency or from unknown causes. In the case of cats, pancreatitis occurs at a prevalence rate of about 0.15% to 3.5% and may account for some cases of poor fat digestibility. Diffuse intestinal diseases, such as intestinal lymphoma, small intestinal bacterial overgrowth, inflammatory bowel disease and liver disease, may also lead to reduced nutrient absorption in the small intestine.

Cases of pancreatic insufficiency are sometimes treated in veterinary practice by the addition of raw pancreas to the diet of the animal. The pancreas should not be heated to avoid denaturation of digestive enzymes. This kind of procedure is not convenient for the pet owner to have to perform on a regular basis. Commercially made enzyme supplements, for example as sold under the trade name Viokase V (believed to be a trade mark of Axcan Pharma US, Inc. of Birmingham, Ala.), are effective in improving fat digestibility in animals affected by pancreatic insufficiency, but they are expensive when given in the requisite amounts. They are therefore unsuitable for inclusion in the regular diet of a pet.

Nicholson et al (op. Cit. disclosed that dietary pancreatic extract supplementation of cats presenting with poor fat digestibility almost doubled fat digestibility, although enzyme supplementation failed to increase fat digestibility to normal levels in all three cats tested. These findings point to pancreatic enzyme supplementation being able to achieve a partial correction.

Suzuki et al (Suzuki A, Mizumoto A. Rerknimitr R, San M G, Dimaano E P. Effect of Bacterial or Porcine Lipase with Low- or High-Fat Diets on Nutrient Absorption in Pancreatic-Insufficient Dogs. Gastroenterology 1999; 116:431-437 The American Gastroenterological Association) studied the effects of bacterial lipase, porcine lipase and diets on protein absorption (inter alia) in pancreatic-insufficient dogs. They concluded that high-fat and high-protein diets optimize fat absorption with both enzymes and proposed to study the effects in humans.

International patent publication WO01/62280 discloses compositions that include crosslinked lipase crystals that are highly resistant to proteolysis and acid degradation. It recognizes that fat-soluble vitamin deficiency, for example vitamin E, is but one of the commonly observed consequences of fat malabsorption.

The prior art does not address the problem of vitamin E deficiency in a dietary framework. Nor does it suggest a dietary solution for prevention of vitamin E deficiency or conditions related to it.

For purposes of this specification, the term lipid fraction should be understood to mean a group of compounds that are insoluble in water, the group embracing fats, oils, waxes, phosphatides, cerebrosides, sterol, terpenes and the like, most of these including a fatty acid in their structures. Lipids can function to carry or transport a nutrient from a food source to the intestine and to the site of utilization, such as in a cell of the recipient's body.

"Digestion", as used in this specification, means the process of breaking down a complex food matrix into its constituent parts, for example fats to glycerol and fatty acids. The breaking down process is primarily by action of gastric, hepatic and pancreatic enzymes.

"Absorption" as used in this specification, means the passage of the products of the breaking down process across the intestinal wall into the blood stream.

"Digestibility", as used in this specification, means the quantity, expressed in percentage form, of a nutrient that is digested and absorbed in relation to the total nutrient quantity ingested by the animal.

"Assimilation", as used in this specification, means the process of incorporation of simple molecules, produced from food digestion and absorbed into the body, into the complex compounds forming the constituents of the organism.

It is thus an object of the invention to provide a nutritional product that, when administered to a pet having sub-optimal serum levels of vitamin E, improves the digestibility of lipid and lipid-linked compounds, enabling more effective absorption or assimilation of vitamin E. Another object is to provide the pet and pet owner with advantages associated with effective assimilation of vitamin E.

A further object is to provide a complete pet food or supplement for a complete pet food that provides dietary means to aid a pet animal to absorb vitamin E.

Another object of the invention is to provide a method of improving vitamin E absorption in a pet animal, especially a senior pet.

A further object is to provide a means of improving the transportation of vitamin E into the a pet's tissues.

SUMMARY

The invention provides compositions and products that include them, for improving or maintaining absorption of vitamin E in a pet animal.

Thus, according to a first aspect of the invention, a method of improving or maintaining absorption of vitamin E in a pet animal includes the step of feeding the pet an edible composition that promotes or maintains or improves its lipid absorption capacity.

In a preferred form of the invention, the composition comprises one or more of a pancreatic function-promoter, a liver function-promoter, and an intestinal mucosa function-promoter.

In an embodiment, the pancreatic function-promoter may comprise a lipase, a gut pH modifier or a pancreatic extract.

The gut pH modifier may include one or more of an acidifier, an alkalanizer, a buffer, a prebiotic or a probiotic microorganism.

The liver function-promoter is preferably selected from taurine, emulsifiers, vitamins, minerals, glutathione and glutathione promoters, and combinations thereof.

In an embodiment, the liver function-promoter is a nutrient that increases endogenous glutathione after ingestion.

The intestinal mucosa function promoter may include a fat transportation aid, agent or carrier. In an embodiment, the aid, agent or carrier is selected from whey protein and proteases having the capacity to promote the formation of lipoproteins.

In a further embodiment, the intestinal mucosa function-promoter includes an anti-inflammatory agent, lactoferrin, a prebiotic or a probiotic micro-organism. It may include a combination of these. The anti-inflammatory agent may be an omega-3 fatty acid.

In a preferred embodiment, the fat transportation aid, agent or carrier has a fatty acid profile selected to improve intestinal absorption. The fatty acid profile is preferably polyunsaturated.

In a still further embodiment, the fat transportation aid, agent or carrier comprises whey protein.

In a preferred form of the invention, the composition is administered as a nutritionally balanced, ready-to-eat meal. The meal may be wet or dry. If dry, the meal may comprise a dried pet food kibble, or a plurality thereof. The meal is preferably administered daily. The composition may, however, be administered as a meal supplement. The meal supplement may be provided in the form of a treat.

According to a second aspect of the invention, a method of maintaining or improving the serum vitamin E level in a pet animal comprises the step of feeding the pet animal an edible composition that promotes or maintains or improves its lipid absorption capacity.

In a preferred form of the invention, the composition comprises one or more of a pancreatic function-promoter, a liver function-promoter, and an intestinal mucosa function-promoter.

The intestinal mucosa function promoter may include a fat transportation aid, agent or carrier.

The fat transportation aid, agent or carrier preferably has a fatty acid profile selected to improve intestinal absorption.

In a third aspect of the invention, a composition for use in improving or maintaining absorption of vitamin E in a pet animal includes a component selected from the group consisting of pancreatic function promoters, liver function-promoters, intestinal mucosa function promoters and combinations thereof, in an amount effective to promote or maintain or improve the lipid absorption capacity of the said pet.

In an embodiment, the composition is administered as a nutritionally balanced, ready-to-eat meal. The meal may be wet or dry.

In an embodiment of the invention, the liver function-promoter comprises a pancreas extract. In a preferred embodiment, the extract includes pancreatic lipase.

In an embodiment of the invention, the pancreas extracts comprise lipase derived from a non-pancreatic source. In an embodiment, the non-pancreatic source is a fungus.

In an embodiment, the composition is prepared in an industrial process and packaged as a ready-to-eat meal.

In an embodiment, the lipid absorption-promoting component is provided in a container for addition to a separately packaged complete meal or for administering apart from a meal. In an embodiment, the component is provided in a pharmaceutically acceptable carrier.

The invention extends, in another aspect, to the use of a lipid digestibility-enhancing component in the manufacture of a dietary composition or dietary supplement, for the provision of a benefit relating to vitamin E absorption in a pet animal. The benefit may be any one of those listed above.

According to another aspect of the invention, a method of improving the appearance of a pet comprises the step of increasing its serum vitamin E level by feeding the pet a diet that contains an agent selected from:
 a fat emulsifier/emulsification system
 an acidifying agent
 a fat transportation agent (whey protein as a carrier for lycopene), and
 combinations thereof.

An advantage of the invention is that it produces visible improvements in the body condition of senior pets, such as fragile senior cats.

Another advantage is that it provides an improvement of a pet's nutritional status. Through this, there are further benefits expected, such as improvement in the quality of life and extended longevity of the pet and greater satisfaction of the owner.

Additional features and advantages are described herein, and will be apparent from the following Detailed Description and the figures.

BRIEF DESCRIPTION OF THE FIGURE

FIG. 1 is a graph tracking the relationship between lipid digestibility and serum vitamin E level in pet cats.

DETAILED DESCRIPTION

It has been found that in pet animals, the absorption of lipid is highly correlated with the absorption of other essential nutrients, for example vitamin E. Hence, a pet with low lipid digestibility is susceptible to deficient or sub-optimal nutritional status, which can compromise its health.

This invention seeks to provide means of prevention and relief for pets that are susceptible to develop, or that have already developed, a vitamin E deficiency as well as to provide a means for increasing serum levels of vitamin E. The invention provides a means for increasing lipid absorption through nutrition management and thereby to increase vitamin E uptake in the gut. Such management can be carried out by the pet owner, care giver or keeper. By implementing it as a regimen that maintains, improves, promotes or otherwise enhances vitamin E assimilation, various health and wellness benefits can ensue. These are set out more fully below.

Thus, a nutrition management regimen for maintaining, improving, promoting or otherwise enhancing absorption of vitamin E in a pet animal, comprises a lipid absorption-promoting ingredient for feeding regularly to the pet animal in need thereof, according to predetermined directions. The lipid absorption-promoting ingredient comprises at least one nutrient selected from the groups comprising pancreatic function promoters, liver function promoters, intestinal mucosa function promoters and combinations thereof. It may be administered as a part of its regular diet, such as in the medium of a nutritionally balanced pet food or as a supplement to a meal or to a treat. The meal may be a wet meal or a dry meal, preferably for daily administration.

The pet may be a cat or a dog. The invention has particular advantage for elderly or senior pets. Generally, these are pets of age 9 years and above.

Pancreatic function promoters that may be used in this invention include natural and artificial lipases, gut pH modifiers, pancreatic extracts, and combinations thereof.

Advantageously, where the pancreatic function promoter is lipase enzyme, it is present to be administered to the pet in an edible composition in an amount sufficient to provide the pet receiving it with from about 1,000 to 80,000 IU of lipase enzyme daily. Preferably, the composition contains sufficient amount of the promoter to provide from about 9,000 to 60,000 IU of lipase enzyme daily, when administered according to a predetermined regimen.

Where the pancreatic function promoter is a gut pH modifier, it may comprise a system that includes one or more of an acidifier, an alkalanizer, a buffer, a prebiotic or a probiotic micro-organism. Preferred gut pH modifiers are those that promote fermentation and modify gut pH in a predictable and controllable manner. Examples of suitable acidifiers are citric acid and lactic acids. An example of a suitable base is sodium hydroxide. The base may also be a carbonate or bicarbonate or include combinations thereof.

In embodiments where the gut pH modifier is an acidifier, it should be provided to be present in sufficient amount to reduce the gut pH by about 1 point on the 14 point pH scale.

In embodiments where the gut pH modifier is an alkalanizer, it should be provided to be present in sufficient amount to increase the gut pH by about 1 point on the 14 point pH scale.

Where the gut pH modifier is a buffer, it should be provided to be present in sufficient amount to maintain gut pH below about 4 during the initial stages of digestion.

Where the pancreatic function promoter is a pancreatic extract, the extract preferably includes pancreatic lipase. However, lipase derived from a non-pancreatic source may, in addition or alternatively, be used.

In preferred embodiments of the invention, the gut pH-modifying agent is a prebiotic or a probiotic micro-organism, or a combination thereof. The prebiotic may be obtained from any suitable natural or purified source, for example chicory, and may comprise inulin or an oligosaccharide. Should a probiotic microorganism be selected, it needs to be one that, via fermentation processes in the gut, regulates the gut pH. In general, probiotic microorganisms produce organic acids such as lactic acid and acetic acid which inhibit the growth of pathogenic bacteria such as *Clostridium perfringens* and *Helicobacter pylori*. Examples of suitable probiotic microorganisms include yeasts such as *Saccharomyces, Debaromyces, Candida, Pichia* and *Torulopsis*, molds such as *Aspergillus, Rhizopus, Mucor,* and *Penicillium* and *Torulopsis* and bacteria such as the genera *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*. Specific examples of suitable probiotic microorganisms are: *Saccharomyces cereviseae, Bacillus coagulans, Bacillus licheniformis, Bacillus subtilis, Bifidobacterium bifidum, Bifidobacterium infantis, Bifidobacterium Ion gum, Enterococcus faecium, Enterococcus faecalis, Lactobacillus acidophilus, Lactobacillus alimentarius, Lactobacillus casei* subsp. *casei, Lactobacillus casei Shirota, Lactobacillus curvatus, Lactobacillus deibruckii* subsp. *lactis, Lactobacillus farciminus, Lactobacillus gasseri, Lactobacillus helveticus, Lactobacillus johnsonii, Lactobacillus reuteri, Lactobacillus rhamnosus (Lactobacillus* GG), *Lactobacillus sake, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus,* and *Staphylococcus xylosus*. The probiotic microorganisms may be in powdered, dried form; especially in spore form for microorganisms which form spores. Further, if desired, the probiotic microorganism may be encapsulated to further increase the probability of survival; for example in a sugar matrix, fat matrix or polysaccharide matrix. Alternatively, the microorganism may be provided as a separately contained supplement to the main food composition.

In an embodiment of the invention, a combination of any of the above two or more pancreatic function promoters may be used.

Liver function promoters suitable for use in this invention may be selected from edible emulsifiers, taurine, glutathione or glutathione promoters, minerals and vitamins. The taurine used may be natural or from a purified source or may be a mixture of both. In embodiments of the invention where the composition of the invention is made available in the form of a dry pet food, taurine is included at up to about 0.5% by weight on a dry matter. (DM) basis. In preferred embodiments, the taurine concentration is in the range from about 0.1% to about 0.4% by weight on a DM basis. In the case of a wet (canned) pet food, the taurine concentration may be up to 1% by weight on a dry matter basis, but is preferably no more than about 0.8% on a DM basis, by weight. In a preferred embodiment, the taurine concentration is from about 0.2% to 0.8% by weight.

Non-limiting examples of glutathione promoters are selenium and vitamin E. In preferred embodiments, selenium is present at about from 2 to 3 times the Association of American Feed Control Officials (AAFCO) minimum. For example, there may be about 0.3 mg selenium per kilogram of diet on a DM basis. Vitamin E levels may be up to about 20 times the AAFCO minimum, for example currently up to about 600 IU on a DM basis. These agents may be obtained from natural or purified sources and may comprise combinations of both.

In an embodiment, the liver function promoter is a nutrient that is capable of increasing endogenous glutathione after ingestion.

The liver function promoter may also be an edible emulsifier. A preferred example is lecithin, which may be obtained from a source such as soya, sunflower oil, wheat germ, egg, avocado and combinations thereof. In preferred embodiments, the composition includes up to about 1% by weight of lecithin on a DM basis when administered in pet food form, or provides up to about 1% of lecithin in the diet, when determined on a DM basis.

Where the liver function promoter is a vitamin, it may for example be obtained from a natural source, for example yeast, or a purified source, or combinations thereof. In preferred embodiments, the composition of the invention comprises a selected vitamin in sufficient amount to exceed the minimum level set from time to time by AAFCO by about 2 to 5 times (in other words about 200-500% of the AAFCO minimum).

Similarly, minerals used for promoting liver function are obtainable from natural or purified sources and combinations thereof. In preferred embodiments, the composition of the invention comprises a selected mineral in sufficient amount to exceed the minimum level set from time to time by the Association of American Feed Control Officials (AAFCO) by about 3 to 5 times (in other words about 300% to 500% of the AAFCO minimum).

Advantageously, the liver function promoter is present to be administered to the pet in an edible composition in an efficacious amount when administered according to a predetermined regimen, in order to obtain at least one of the benefits set out below.

The intestinal mucosa function promoter of the invention may, in an embodiment, include a fat transportation aid agent or carrier, such as whey protein or a protease to help the formation of lipoproteins. An example of a suitable protease is papain. The diet or dietary composition may preferably comprise from about 0.1% to 1% by weight of papain on a DM basis. Should whey protein be included as a lipoprotein formation promoter, it is preferably present in concentrations from about 2% to 10%, preferably about 5% to 7%, by weight of the diet on a DM basis.

The intestinal mucosa function promoter may, however, alternatively or in addition, include an anti-inflammatory agent. Suitable examples of these are the omega-3 fatty acids, lactoferrin, prebiotics, probiotic micro-organisms or fatty acids that have a profile specially selected to improve absorption. By way of example, a fatty acid group with a suitable absorption-enhancing profile is the polyunsaturates. In preferred embodiments, these are included in the diet at about 2% to 25%, preferably about 7% to 19%, by weight of the diet on a DM basis. Preferably, they are derived from fish oils.

Advantageously, the intestinal mucosa function promoter is present to be administered to the pet in an edible composition in an efficacious amount when administered according to a predetermined regimen in order to obtain at least one of the benefits set out below.

Where the intestinal mucosa function promoter comprises an omega 3 oil, it is preferably included in the diet from about 1% to 20%, preferably about 3% to 16% by weight on a DM basis. Where the diet or composition comprises lactoferrin, it is preferably included from about 100 mg to 200 mg per day. In the case of chicory, in preferred embodiments, it comprises from about 0.5% to 2% by weight of the diet or dietary composition on a dry matter basis. Prebiotics, for example inulin and/or oligosaccharides, should preferably make up from about 0.1% to 1% by weight of the diet on a DM basis. Probiotics, when included, are preferably at a numerical concentration of at least about $10^5$ CFU in the diet.

The benefits that the feeding of the composition according to the method of the invention may achieve in a pet, may be related to gut function, outward appearance, aging, or to more general health aspects. Benefits relating to gut function include Increased nutrient and energy digestibility,
Improved gut microflora as may be manifest in decreased small intestine bacterial overgrowth ("SIBO"),
Improved fecal consistency and less offensive odor,
Optimal fecal volume,
Reduced flatulence,
Improved gut detoxification, and
Improved regularity of food transit time.
Appearance Related Benefits May Include Improved body condition and muscle tone,
Improved skin and coat condition, brought about by improving the bioavailability of required nutrients, such as fatty acids and vitamins, and
Improving the overall appearance of senior pets by making them look younger.
Aging Related Benefits May Include:
A delayed onset of signs of aging,
Reduction or amelioration of the effects of aging,
Restoration of functionality of the digestive system in the aged pets, and
Increased longevity.

The signs of aging may, for example, be appearance-related, such as greying of the coat, or activity-related, such as lower levels of activity. The effects of aging may be related to movement, such as apparent joint stiffness, or digestion-related, or reduction of sensory capacity and the like.

Owner-Interaction Benefits May Include
Improved physical activity,
Increased level of playfulness,
Improved alertness, mental performance and cognitive ability, and
Improved pet-owner interaction and bonding through increased activity and playfulness of the pet.
More General Health Benefits that are Provided by the Invention Include
Improved water turnover,
Improved nutritional and overall health status,
Improved antioxidant status by increasing vitamin E absorption,
Improved nitrogen balance,
Improved absorption of all lipid-soluble nutrients, for example fatty acids, vitamins A, D, E and K,
Reduced renal overload by reduction of proteolysis, and
Improved functions associated directly or indirectly with improved absorption of fat or antioxidants.

The invention thus also provides a method of reducing the effects of vitamin E deficiency in a pet. The steps of this method may include administering to the pet a diet comprising an effective amount of an ingredient that maintains, promotes or enhances the capacity of the pet to digest lipid efficiently. The ingredient may be selected from those named above and belonging to the general categories of pancreatic function promoters, liver function-promoters and intestinal mucosa function-promoters.

By improving the capacity of a pet animal to absorb a lipid or lipid fraction that is a carrier of an essential nutrient, the capacity of the animal to absorb the vitamin E, as well as other essential nutrients, is also improved. Such essential nutrients are typically vitamins such as vitamin A, D, or K and arachadonic acid (ARA). Through enhanced absorption efficiency of these nutrients, for example vitamin E, the serum level thereof may be maintained and/or improved. FIG. 1 illustrates the relationship that has been found to exist between fat digestibility, expressed as a percentage (%), and serum vitamin E (yg/ml).

The digestibility enhancing ingredient or agent may be used in a method of manufacturing a dietary composition or supplement or pharmaceutical composition for providing benefits associated with optimal lipid absorption in a pet animal, or for the prophylaxis of conditions associated with poor lipid absorption and low digestibility. Such methods are described further in the paragraphs that follow.

The lipid assimilation or digestion-promoting ingredient, whether provided alone or in an ingredient combination or in a system of synergistic ingredients, may be provided for administering to a pet animal in need thereof in any of a number of different forms. For example, it may be fed to the pet as part of a ready-to-eat meal or as part of a treat. Where provided as a pet food meal, the pet food of the invention may be produced in wet or dry form, using any suitable process. Preferably, the ingredients will be part of a nutritionally balanced meal. They may also be provided as a treat for feeding in addition to regular meals, or as a dietary supplement or complement that may be administered with a meat or a snack or treat. The ingredient or ingredients may also be administered in a pharmaceutical form, the ingredient being contained in a pharmaceutically acceptable carrier. Such forms include tablets, capsules, syrups, drinks and gels and the like, in which the ingredients are suitably storable until the occasion of use.

Where, in a non-limiting example, ingredients are provided in the form of a pet food in wet form, it may be delivered as an emulsion gel or as solid pieces in a flowable gravy or gel.

Thus, to produce a thermally gelled emulsion that will set upon cooling, a suitable meat material is comminuted to produce a meat batter. Suitable gelling agents, for example starches and gums such as kappa-carrageenan, locust bean gum, guar gum, and xanthan gum may be added to the meat batter. Usually no more than about 1% by weight of gum is needed.

Water may also be added the meat batter to provide from about 70% to about 85% by weight of moisture. If sufficient moisture is present in the meat material, water need not be added.

The meat batter is then heated to a temperature suitable to initiate thermal gelling of the mixture; for example a temperature of about 40° C. to about 65° C. in a mixer-cooker. Steam may be injected into the meat batter if desired. The heated meat batter may be emulsified if desired. The meat batter is then maintained at a temperature of about 40° C. to about 65° C. until needed. After retorting and cooling to room temperature, the meat batter forms a thermally gelled emulsion that is substantially solid or at least holds its form.

To produce solid food pieces in gravy or gel, solid pieces of meat or other material, or both, may be mixed with a gravy. Solid pieces of other materials may also be used; such as rice grains, pasta or noodles, vegetable pieces, and the like.

The solid food pieces may be in the form of pieces of a thermally gelled matrix. The pieces of the thermally gelled matrix may be produced by any suitable procedure, for example the procedures described in any one of U.S. Pat. Nos. 4,781,939, 5,132,137 and 5,567,466 and PCT application WO 97/02760.

The thermally gelled matrix may be formed in suitable equipment such as an emulsion mill or an extruder to form pieces or chunks. If an extruder is used, the emulsion may be forced through an orifice to provide the emulsion with a desired shape; for example of oval, square or rectangular cross-section. The extrudate may then be cooked in a suitable continuous cooking system; for example a tunnel oven using hot air, steam, mixtures of hot air and steam, or microwaves as the heating medium. The core temperature of the extrudate is raised such that the extrudate undergoes thermal gelling. For example, the core temperature may be raised to at least about 80° C.; for example about 85° C. to about 95° C. The gelled extrudate may then be cut into pieces and the pieces cooled to provide pieces of a thermally gelled matrix. The pieces may be subjected to flaking if desired. Cooling may be carried out by spraying water on the pieces. Alternatively, other cooling media may be used.

If a gravy is used with the solid food pieces, it may be produced from water, one or more starch or gums, and suitable flavoring agents. The gravy preferably comprises about 20% to about 80% by weight of the mixture of solid pieces and gravy. Suitable gums are kappa-carrageenan, locust bean gum, guar gum and xanthan gum.

If a gel is used with the solid food pieces, it may be produced from a suitable gelling agent, water and suitable flavoring agents. The gel preferably comprises about 20% to about 80% by weight of the mixture of solid pieces and gravy. Suitable gelling agents are proteins such as gelatin; gums such as alginates, kappa-carrageenan, locust bean gum, guar gum and xanthan gum, and the like. The gel or aspic may be prepared as is conventional.

Combinations of the processes described above may also be used. For example, a thermally gelled emulsion may be prepared as described above. Then solid food pieces, which may be pieces of a thermally gelled matrix, meat pieces, vegetable pieces, combinations of these pieces, and the like, are combined with the thermally gelled emulsion. As a further alternative, combinations of thermally gelled emulsions and solid food pieces in gravy or gel, may be used. Suitable combinations are described in WO 98/05218 and WO 98/05219; the disclosures of which are incorporated by reference.

The pet foods are then filled into cans or other containers, the containers sealed, and the products retorted in the normal manner. Suitable equipment is commercially available.

A suitable process for manufacturing dried pet food involves cooking a feed mixture of the various ingredients, forming the cooked mixture into pellets, drying, and then coating the pellets with flavors. The cooking and forming steps are preferably carried out using an extruder, as is well known in the art. However, the pellets may be produced by other cooking procedures such as baking a preformed food body comprising the selected ingredients, preferably in nutritionally balanced proportions.

Whichever process is utilized, the lipid assimilation-promoting ingredient may be added at a suitable stage. Whichever stage is decided on may depend on the nature of the ingredient. It may be added to the major ingredients prior to the cooking, heating or extrusion stages, or, in the case of heat-sensitive ingredients, may be added after the pieces have already formed, whether they be wet or dry. The ingredient may be absorbed into the food body, to be contained therein, or be injected, or be coated to remain largely on the surface. It may be included in the gravy that may accompany a'gelled or extruded chunk, or be provided as a meal supplement.

Generally, application of the functional ingredient in a post-kibble formation step is carried out after the extrusion, drying and cooling process stages. The pet food kibbles enter a coating station, equipped for example with a coating drum. Here one or several coating systems are applied in liquid and/or in powder form to adjust the nutritional profile to physiological and legal requirements, by including or adding such ingredients as required vitamins, fat, minerals and trace elements, to enhance the product palatability and to improve product cosmetics.

The amount of the pet food to be consumed by the pet to obtain a beneficial effect will depend upon factors such as the size or the pet, the type of pet, activity level and the age of the pet. However, an amount of the nutritional composition to provide a daily amount of about from 10 g/kg to 25 g/kg of body weight of the pet, on a dry matter basis, should be administered. Preferably, the amount should be in the range from about 12.5 g/kg to 20 g/kg of body weight on a DM basis in the diet.

Accordingly, the appropriate amount of the ingredient may then be included in the meal or treat, according to the pet's dietary requirements. The ingredient may be mixed in with the base formulation and then processed, or mixed into a gravy or other carrier for including with or adding to the food or treat.

It is believed that by providing a pet food composition as provided for above, making it available to minders or owners of elderly pets and drawing attention to the prospect that regular feeding of the composition to such pets can bring about at least a temporary alleviation of symptoms indicative of poor lipid assimilation in their pet, the pet minder will be encouraged to administer the pet the composition on a regular basis. A suitable way of drawing the attention of the minder to the benefits of the composition is by way of notice on the packaging of the food composition, alternatively by separate advertising thereof.

Numerous modifications may be made to the embodiments described above without departing from the scope of the invention. By way of example, and not limitation, trials of products of the invention will now be described for further illustration:

EXAMPLE

A series of digestibility tests is used to scan which nutritional interventions among numerous possibilities may improve the fat digestibility of cats pre-selected for their low fat digestibility (i.e. below 80%) when added to a control cat food diet.

Lipid digestibility is assessed on a group of cats using materials and methods as follows:
  All participating cats are adults and in good health and are not pregnant.
  Each test diet is the only source of nourishment for the cats.
  Water is available to the cats at all times.
  Each cat's weight is recorded prior to the initiation of the test.
  Each cat is fed the amount of food required to cover its metabolizable energy requirements.
  The cats are fed the same control diet for a feces pre-collection period of 5 days.
  Each cat's weight is recorded at day 6.
  The fecal collection period is from day 6 through 15. The food consumed during this period is recorded.
  On day 6, the diet is fed together with red iron oxide as a marker, at a concentration of 1.0 g/kg of meal mass for canned diets and 2.5 g/kg of meat mass for dry diets.
  Red marked feces are the first to be collected. Any unmarked (normal colored) feces on day 6 and 7 prior to the first appearance of the red marked feces are discarded. All red marked feces are collected, as well as all unmarked feces that are passed after the first red feces are observed.
  Collected feces for each cat are stored frozen at −20° C.
  On the morning of day 15, red iron oxide is again added to the diet (as in day 6), this time to mark the end of the trial feeding period, and the weight of each cats is recorded. Feces continue to be collected until the reappearance of the red marker.
  Two samples of the diet and each individual cat's fecal samples are freeze dried and sent for analyses of protein, fat, dry matter, and ash.

Examples illustrating the implementation of fat absorption-improving nutritional intervention into commercial pet food products are now described:

Example 1

Trial Using a Canned Food Diet

In this example, participating cats receive an emulsion meat diet, having a composition of about 9% fat, 2.2% ash, 8.4% protein, and 76% moisture. This is called diet A.

Another diet, called B, is based on a similar formulation, but with the inclusion of the following additional ingredients:
  A pancreatic function promoter: 0.1% Acidifier (citric acid).
  A Liver function promoter: at about 4× AAFCO minimum taurine level for wet cat food (0.8% by weight on a dry matter basis)
  An Intestinal mucosa function-promoter: Fish oils (3%)

A group of 20-cats with low fat digestibility (i.e. less than 80%) is fed both diets, A and B, in a crossover design of two digestibility tests. Each diet is fed for a 15-day digestibility test, the first 5.days being an adaptation period and the remaining 10 days as the fecal collection period. The cats are found to digest a significantly higher percentage of fat when fed diet B than when fed diet A. As a result, total energy digestibility and organic matter digestibility is improved in diet B. Cats are found to need a lower amount of diet B to cover their energy requirements than of diet A. Overall, cats appear to maintain their weight better when fed diet B than when fed diet A.

Example 2

Trial Using a Dry Food Diet

This example uses a conventional dry cat food having a composition of about 31% protein, 15% fat, 4.5% fiber, 12% moisture and 5% ash, called diet C.

Another diet, called D, was based on a similar formulation but the following additional ingredients were included:
  A pancreatic function promoter: Taurine (0.27%)
  A Liver function promoter: Lecithin from Soya (1%)
  An Intestinal mucosa function promoter: Chicory (1%)

In this trial, a group of 20 cats with known low fat digestibility (i.e. less than 80%) is fed diets C and D, in a crossover design of two digestibility tests. Each diet is fed for a 15-day digestibility test, the first 5 days being an adaptation period and the remaining 10 days the fecal collection period. The cats on diet D are found to digest a higher percentage of lipid than those on diet C. Total energy digestibility and organic matter digestibility are also improved with diet D, when compared with diet C. Reduced fecal volume and odor were noted when cats were fed diet D instead of diet C.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A composition comprising:
  taurine ranging between about 0.1% and about 1% by weight of the composition on a dry matter basis,
  fish oil ranging between about 0.1% and 20% by weight of the composition on a dry matter basis, and
  an acid in an amount sufficient to reduce the gut pH of a cat by about 1 point on the 14 point pH scale, wherein the composition provides an amount of the taurine, the fish oil and the acid effective to promote or maintain or improve the lipid absorption capacity of a cat.

2. The composition of claim 1 wherein the acid is selected from the group consisting of citric acid, lactic acid, and a combination thereof.

3. The composition of claim 1 wherein the acid is citric acid.

* * * * *